United States Patent [19]

Steer

[11] Patent Number: 4,890,608

[45] Date of Patent: Jan. 2, 1990

[54] ATTACHMENT ASSEMBLY FOR USE ON THE HUMAN SKIN

[75] Inventor: Peter L. Steer, Surrey, England

[73] Assignee: E. R. Squibb and Sons, Inc., Princeton, N.J.

[21] Appl. No.: 870,592

[22] Filed: Jun. 4, 1986

[30] Foreign Application Priority Data

Jun. 20, 1985 [GB] United Kingdom ................. 8515632

[51] Int. Cl.⁴ .............................................. A61F 5/44
[52] U.S. Cl. .................................... 128/156; 604/332
[58] Field of Search ................................ 128/155–161

[56] References Cited

U.S. PATENT DOCUMENTS

| Re. 29,453 | 10/1977 | Weddle . | |
|---|---|---|---|
| 3,039,464 | 6/1962 | Galindo . | |
| 3,081,771 | 3/1963 | Lee . | |
| 3,522,807 | 8/1970 | Millenbach . | |
| 3,604,421 | 9/1971 | Pizzella . | |
| 3,734,096 | 5/1973 | Millenbach . | |
| 4,095,599 | 6/1978 | Simonet-Haibe . | |
| 4,213,458 | 7/1980 | Nolan et al. . | |
| 4,450,845 | 5/1984 | Engel | 128/132 R |
| 4,488,557 | 12/1984 | Engel . | |

FOREIGN PATENT DOCUMENTS 2396541 3/1979 France .
2119654 11/1983 United Kingdom .

OTHER PUBLICATIONS

A copy of U.S. Ser. No. 681,176, filed 12/13/84 entitled "Ostomy Appliance with Improved Attachment Means".

A copy of the Information Disclosure Statement filed in AR of this sheet 1 along with copies of documents cited therein.

Primary Examiner—C. Fred Rosenbaum
Attorney, Agent, or Firm—Donald J. Barrack; Robert E. Lee, Jr.

[57] ABSTRACT

An attachment assembly is disclosed for attaching an article such as a wound cover or a prosthesis to human skin. The article attached may be, for example, a cover or dressing over a wound or a fistula or other lesion, it may be an eye patch or a breast prosthesis for use after masectomy or it may be a pouch to cover the genital region. The attachment assembly comprises a body-attachable pad of skin-compatible adhesive material and a series of double-sided adhesive layers thereon, which layers are constructed and arranged to be manually peeled off one-by-one when desired in order to expose a fresh adhesive surface to which the article is then attached.

6 Claims, 9 Drawing Sheets

ATTACHMENT ASSEMBLY FOR USE ON THE HUMAN SKIN

BACKGROUND OF THE INVENTION

This invention relates to an attachment assembly for attaching an article such as wound cover or a prosthesis to human skin. The article attached may be, for example, a cover or dressing over a wound or a fistula or other lesion, it may be an eye patch or a breast prosthesis for use after mastectomy or it may be a pouch to cover the genital region. In a particular embodiment the invention relates to wound management appliance; pad for same; attachment means for same; and kit of parts for assembling same.

SUMMARY OF THE INVENTION

According to the broadest aspect of the present invention an attachment assembly for attaching an article to the human skin comprises a body-attachable pad of skin-compatible adhesive material and a series of double-sided adhesive layers thereon, which layers are constructed and arranged to be manually peeled off one-by-one when desired in order to expose a fresh adhesive surfaces to which the article is then attached.

For simplicity of description herein, the following description relates principally to the attachment of a wound cover to a person having a wound or lesion, but the same method and apparatus may be employed for attaching any of the articles referred to above.

The present invention is not concerned with attachment of an ostomy appliance to a wearer; for details concerning this the reader is referred to our co-pending U.S. patent application Ser. No. 681,176, filed 12/13/84, U.K. Patent Application No. 84 15610 and to European Application No. 146367 to be published on 26th June 1985.

According to the one embodiment of the present invention, there is provided a wound management appliance comprising a body-attachable pad of skin-compatible adhesive material which can have an orifice cut therein, the pad then being capable of surrounding the wound, and means whereby a plurality of wound covers can be attached in sequence to the pad by exposing a fresh region of adhesive each time it is desired to attach a fresh wound cover.

According to another embodiment of the invention there is provided a wound management appliance comprising a medical grade adhesive pad for attachment to the skin surrounding a wound, and a plurality of double sided adhesive annuli separated by sequentially peelable cover annuli and carried by the pad, each of the double sided adhesive annuli having a peripherally projecting portion serving as a gripping tab.

The double-sided adhesive annuli are intended for sequential use in attaching a wound cover, via a flange thereon, to the pad of medical grade adhesive material which the wearer has attached to his (or her) skin surrounding the wound. The reason for having a plurality of adhesive layers separated by peelable cover annuli is so that a new double sided annulus can be exposed by peeling off the outer cover layer. Hence each time a wound cover is changed it can be securely reattached to the medical grade adhesive pad and there is no need to frequently remove the pad. This is a considerable advantage in that the operation of removing and replacing such a pad is one of some difficulty and is often painful.

Such an appliance can be used as a 4-day or a 5-day wound management appliance by providing a corresponding number of double sided adhesive annuli. Each peelable cover annulus may have a radially projecting finger tab which serves two purposes, firstly it can carry a number or indication (e.g. "Monday") and secondly it enables the peelable cover annulus to be readily stripped off to expose the adhesive surface of the underlying double sided adhesive layer so that the flat surface of the flange on the bag can be brought into face-to-face contact with the so exposed adhesive surface.

In accordance with one preferred embodiment of the invention, a wound cover is attached to a body-attachable pad by a series of sequentially peelable adhesive members each of which has a grasping tab. A flexible microporous layer or tape may be used to assist in attaching the pad to the skin of the wearer. In one embodiment the tabs are arranged so that peeling off a first tab exposes a second tab, the latter not being accessible to the user until the first tab has been peeled off. In another embodiment the tabs are radially extending and angularly spaced apart from tabs of adjacent adhesive numbers.

Alternatively, double sided adhesive layers may be alternated with peelable cover layers, and the cover layers may be shaped and arranged so that they are sequentially peelable, that is to say, each cover layer has a grasping tab and these tabs are so arranged that peeling off one tab exposes an underlying tab. Each cover layer is peeled off when it is desired to expose a fresh region of adhesive in order to attach a fresh wound cover to the pad of skin-compatible material which is adhesively attached to the region of the skin surrounding the wound.

In accordance with further alternative embodiment of the invention, a kit of parts for making a wound management appliance includes an apertured pad of body-attachable, skin-compatible material, and a plurality of wound covers to each of which is attached a peelable cover layer which when removed exposes an annular region of adhesive on a flange of the wound cover, the said region of adhesive being arranged in use to adhesively secure each wound cover in turn to the pad.

In hospital use, a hole equivalent in area to the wound is cut in the pad of skin compatible material. A like area of a plastics backing material is also removed; then when the member is applied to the body an inner marginal edge portion of the pad takes up a portion closely surrounding the edge of the wound and forms both a protective pad and a seal.

The invention will be better understood from the following non-limiting description of examples thereof given with reference to the accompanying diagrammatic drawings in which:

BRIEF DESCRIPTION OF THE DRAWINGS

FIGS. 15 and 16 illustrate an example of a pad of medical grade adhesive, FIG. 15 being a cross-sectional view taken in a vertical plane and FIG. 16 is a front view of a plaster with sequentially strippable portions applied to the body-attachable member shown in FIG. 15;

DETAILED DESCRIPTION OF THE DRAWINGS

In the drawings, like parts bear like reference numerals.

Figure 1:
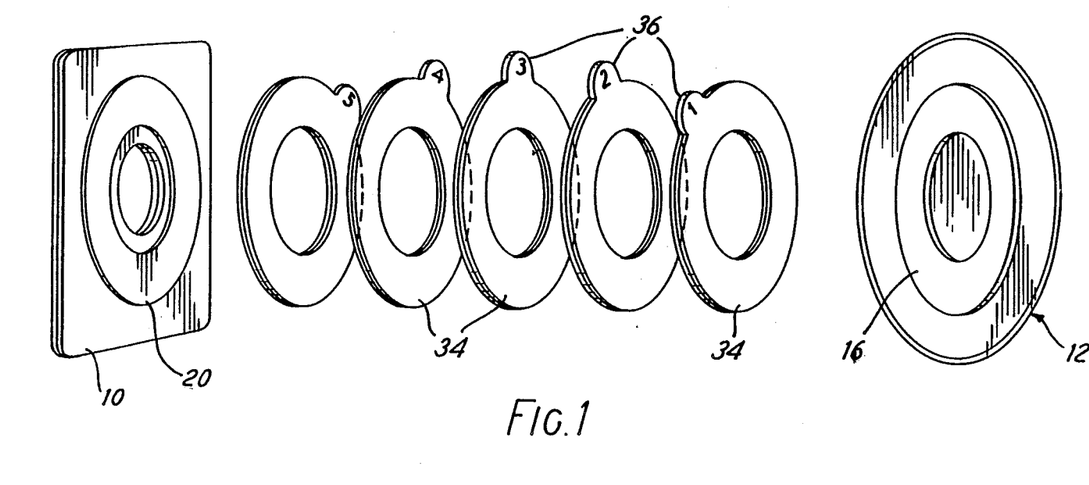
FIG. 1 is an exploded perspective view of a medical grade adhesive pad, a plurality of double sided adhesive annuli, and intervening cover annuli.
Figure 2:
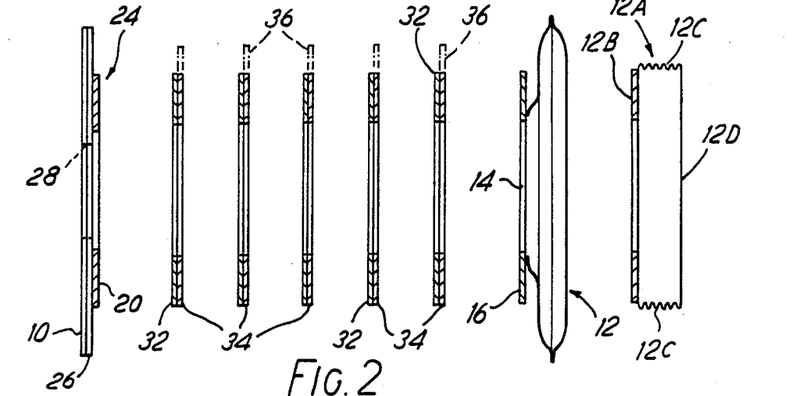
FIG. 2 is a side view corresponding to FIG. 1.

Referring firstly to FIGS. 1 and 2, the illustrated wound management appliance includes a medical grade adhesive pad 10 and a wound cover 12. The wound cover has a flange, e.g. of synthetic plastics material, having an annular flat surface which is intended to face towards the body of the wearer when the appliance is in use. This surface is indicated at 16. The medical grade adhesive pad 10 also has secured thereto a flange 20 which optionally includes an inner peripheral rib not shown. The flange 20 has an outwardly facing flat annular surface 24, intended to receive a stack of double sided adhesive annuli which are interleaved with annular cover layers. The medical grade adhesive pad 10 may be bonded to a plastics film layer 26, in conventional manner. In use, a hole indicated by the dotted lines 28 (FIG. 2) is cut in the pad 10. The size and shape of the hole is cut in accordance with the wound involved. The hole 28 is illustrated as circular but frequently it will be oval or rectangular, and it may be of any shape.

Suitable medical grade adhesives comprise pressure sensitive adhesive formulations that consist of a homogeneous blend of one or more water soluble or water swellable hydrocolloids dispersed in a viscous elastomeric substance such as polyisobutylene as disclosed by Chen in U.S. Pat. No. 3,339,506. Optionally, the adhesive composition can also include one or more cohesive strengthening agents described by Chen et al. in U.S. Pat. No. 4,192,785 or one or more hydratable natural or synthetic polymers as described by Pawelchak et al. in U.S. Pat. No. 4,393,080. Other medical grade adhesives designed for wound care and available on the market are also suitable.

A wound cover 12A is shown at the right hand side of FIG. 2. This is an alternative to the cover 12. The cover 12A is shown in diagrammatic cross-section, the cover being generally circular in shape and the cross-section taken on a vertical central plane intersecting the axis. The illustrated wound cover 12A has a flat rear (body side) surface 12B joined by a bellows-like wall 12C of flexible plastics material to a front wall 12D which may but need not be of the same material. The wall 12D may advantageously be transparent. This facilitates visual inspection of the wound. A gas vent (not shown) may be included. The surface 12B is in use attached to the pad 10 in the manner described herein.

Figure 3:
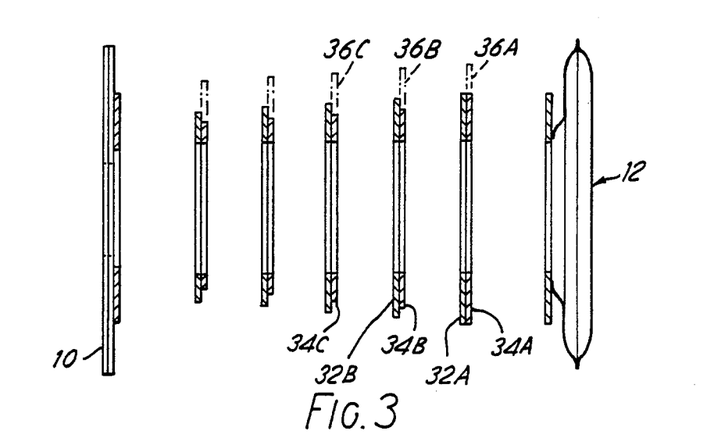
FIG. 3 is a side view of an alternative embodiment of the invention.

The double-sided adhesive annuli are indicated at 32, FIGS. 2 and 3, and for example, five are here shown. This would be appropriate for a 5-day wound care appliance. The fifth one in order of use is directly adhesively attached by one of its adhesive surfaces to the surface 24 and by its other surface to a peelable annular cover layer 34. Like cover layers are located between adjacent double sided adhesive annuli, and these cover layers as seen best in FIG. 1 each have a radially projecting finger tab 36 useful firstly for peeling off the layer 34 and secondly for carrying a numeral or other visible indication to assist the hospital personnel or the user of the appliance.

The wound cover 12 may be a bag which may if desired have a drain outlet not shown. Alternatively, the cover may be of any convenient form. It may be a closed bag intended to be thrown away after use, see FIG. 2 for example.

The words "annulus" and "annuli" are used in the application without a strict geometrical meaning. That is to say, a double sided annulus as used in this invention need not be geometrically circular; a double sided adhesive layer of any shape which surrounds the wound and which can be peeled off from an adjacent layer to expose a region of adhesive would be suitable.

Referring now to FIG. 3, the wound cover 12 and medical grade adhesive pad 10 are as shown previously. The double sided adhesive annuli interleaved with peelable cover annuli however have a gradually diminishing outside diameter as one moves from the first to be used (nearest to the wound cover) to the last to be used (nearest to the pad). The reason for this is to ensure that when one peelable cover layer (e.g. 34A) is removed, it exposes an area of fresh adhesive on the double sided adhesive annulus 32A, and then when the next cover layer 34B is removed, a fresh layer of adhesive on the annulus 32B is exposed. Deterioration of the outer edges of the adhesive annuli is thereby minimized.

Another feature of difference compared to the FIGS. 1 and 2 embodiment is that the outer diameter of the adhesive layers is greater than that of the cover layers (except for the peel tabs thereof). Consequently narrow outer rims of the adjacent adhesive annuli tend to stick together and prevent any peel apart occurring except at the surface where the outermost peel-off cover annulus 5 is being removed.

Figure 4:
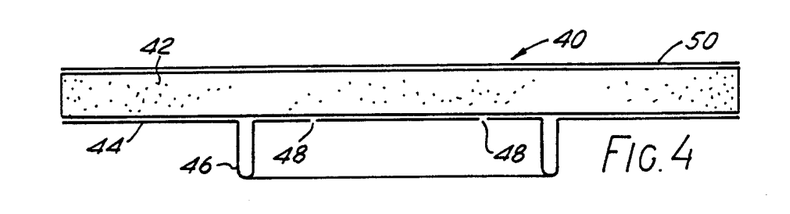
FIG. 4 is a cross-sectional diagrammatic view, somewhat enlarged from full size, of an example of a body attachable member according to the invention.

Referring now to FIG. 4 a body-attachable member or pad 40 comprises a pad 42 of medical grade skin compatible adhesive fixed to a disc 44 of plastics material. The disc 44 has an upstanding rim 46, and a closed loop line of weakening indicated at 48 to define an area within the rim 46 which can readily be removed by a user without the use of a tool.

A strippable protective layer 50 is applied to the rear surface of the pad 52. This layer 50 is stripped off to expose an adhesive surface of the pad 52 when the pad 40 is to be applied to the person's body.

The good adhesive contact between the pad 42 and the skin surrounding the wound provides a sealing effect preventing any migration of wound exudations towards the surrounding skin area. The annular surface 44 of the disc serves for adhesive attachment of a wound cover in any of the various ways described in this patent application.

In a preferred form of the present invention, the rim 46 is produced by vacuum forming. A large number of body attachable members can be readily produced without the need for individual moulding of plastics disks having rim parts.

Figure 5:
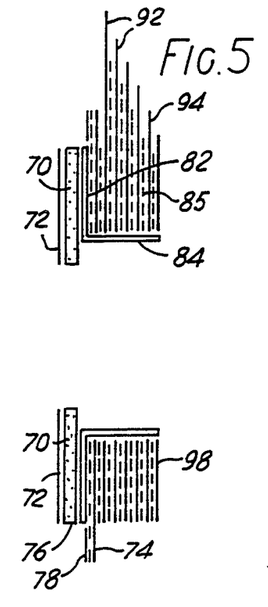
FIGS. 5 and 6 show, in cross-section and in front elevation respectively, one embodiment of a skin-compatible medical grade adhesive pad carrying a plurality of "peel off" adhesive annuli.
Figure 6:
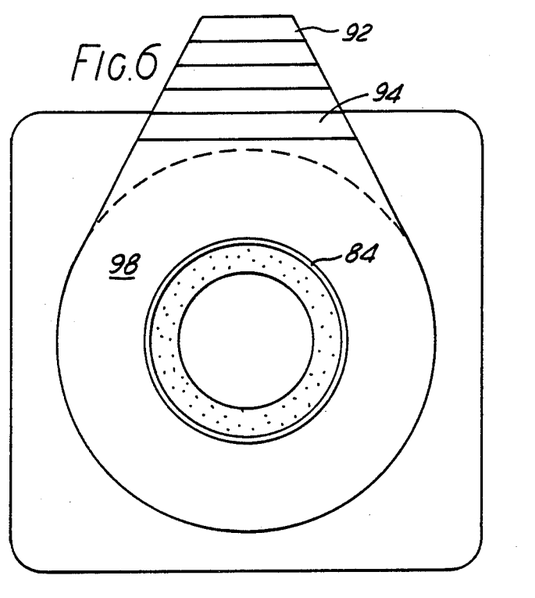

An alternative embodiment of the present invention is illustrated in FIGS. 5 and 6. As seen in FIGS. 5 and 6, a pad 70 of skin-compatible medical grade adhesive material such as that described above, having a central hole and carrying a strippable rear cover layer 72 supports a front cover sheet 74 whose function is to cover over the edges 76 of the pad 70 which would otherwise be exposed, there being a strippable annular paper or like layer 78 which protects adhesive on the rear surface (left hand side as seen in FIG. 6) of the protective layer 74 where this extends beyond the pad 70. As illustrated, the pad 70 is in the form of a flat disc and the protective layer 74 is substantially rectangular. Attached to the pad 70 is a plastics disc 82 carrying a central circular rim 84 which hole is slightly larger than the wound. The disc 82 carries, stacked over the layer 74, a stacked pile of annular adhesive attachment members, herein called plasters, each plaster being constituted by a layer of tough paper or flexible plastics film bearing adhesive 85 and having a grippable tab 92. The tab arrangement as illustrated in FIG. 5 is such that the rearmost plaster has the largest tab and the forwardmost plaster has a relatively small tab as seen at 94. The assembly is protected by a front cover annular layer of release paper or other suitable material which is identified at 98.

It will be seen that by peeling off firstly the cover layer, an annular region of adhesive is exposed to which a new wound cover may be applied, and a later inspection of the wound achieved by peeling off the first adhesive plaster 94, further fresh adhesive on the so-exposed face of the next underlying plaster is made available for attaching a subsequent wound cover to the appliance.

Figure 7:
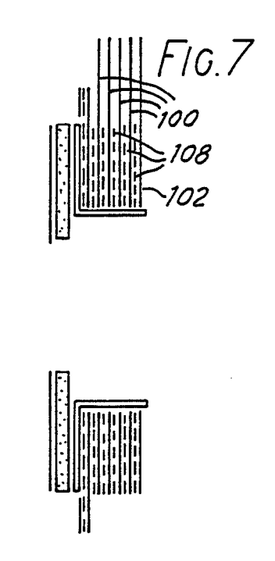
FIGS. 7 and 8 show, in cross-section and in front elevation respectively, a second embodiment of a pad carrying a different arrangement of "peel off" adhesive annuli.
Figure 8:
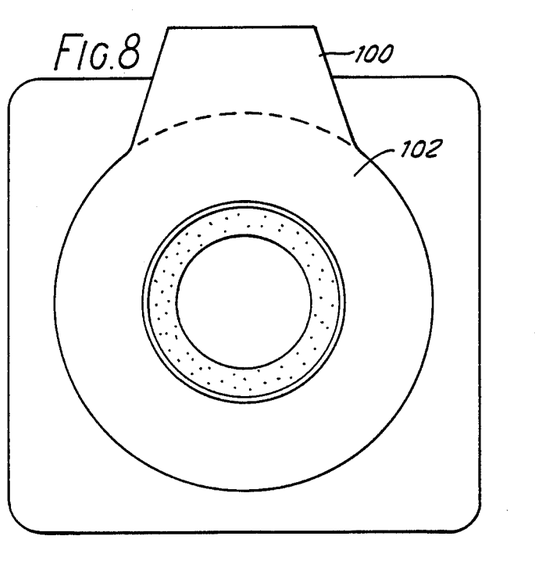

FIGS. 7 and 8 show an alternative version of this embodiment of the invention, the difference being that in this embodiment the tabs of the adhesive plasters 100 are all of the same size. As seen in FIGS. 7 and 8, no adhesive is provided between the plasters outside the annular region, so that one tab can readily be separated from the next and so that the cover sheet 102 can be removed at the beginning of the use of the appliance.

Figure 9:
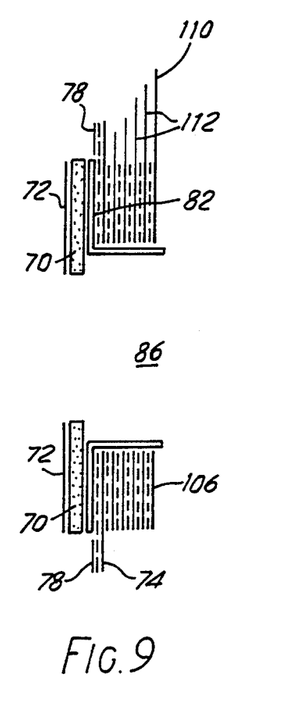
FIGS. 9 and 10 show, in cross-section and in front elevation respectively, a third embodiment of a pad carrying yet another arrangement of "peel off" adhesive annuli.
Figure 10:
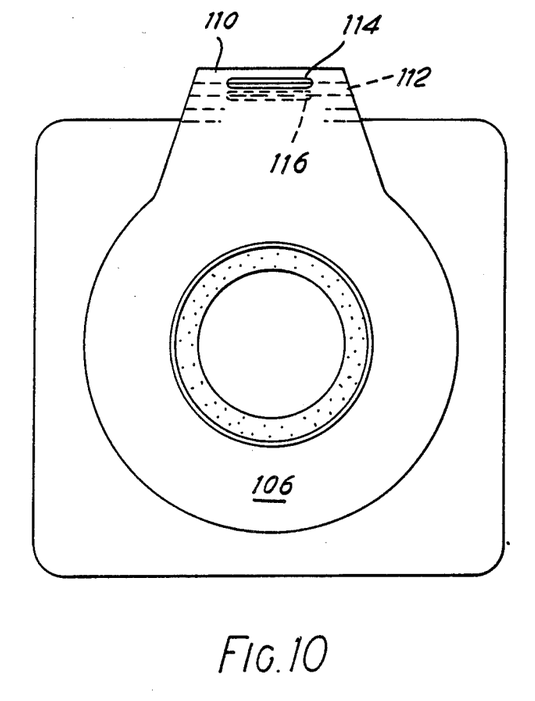

Another variation of this embodiment of the invention is illustrated in FIGS. 9 and 10. According to this advantageous version, each of the cover layers 106 and the plasters 108 is annular in form with an upwardly projecting tab, the tab being denoted 110 in the case of the cover layer and 112 for each of the plasters. Each of the plasters has a tab of progressively increasing height, moving from the plaster closest to the disc 82 to the plaster furthest from the disc 82. Moreover, each tab has an elongated slot cut therein, near to the top of the tab, to enable a user to insert his fingernail in the slots so as to more readily separate one tab from the next. The slot in the cover layer is indicated at 114 and the aperture in the front tab 112 is indicated at 116. For simplicity of illustration in FIG. 10, the apertures in the other tabs 112 are not shown.

Referring to the versions of the invention shown in FIGS. 5-10, it will be realized that any convenient numbers of separate plasters may be employed. Although five plasters have been illustrated in FIG. 5, and four plasters in FIGS. 7 and 9, any selected number of plasters, e.g. one for each day of the week, can be included in the appliance. Moreover, while in some instances it may be preferable for the wound cover which is to be used with the illustrated appliances to have a relatively stiff plastics flange surrounding the stomal orifice in one of its walls, in other instances no such stiff flange would be needed and the wound cover could be adhesively secured directly to the exposed adhesive surface.

Figure 11:
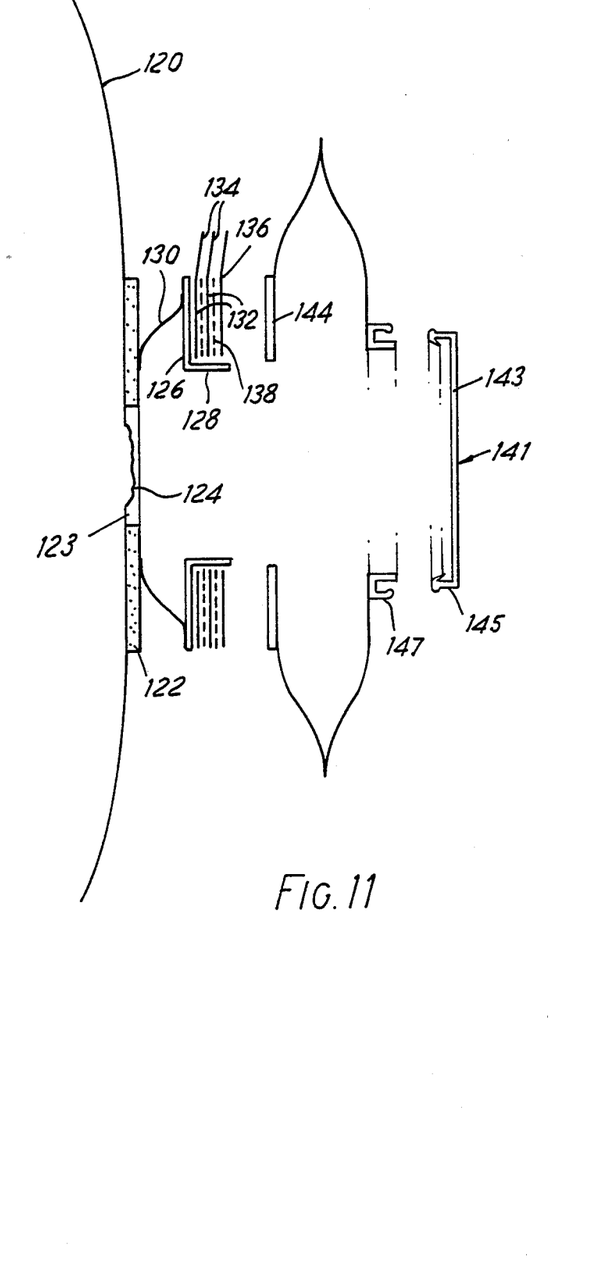
FIG. 11 diagrammatically shows a further embodiment of a body-attachable pad together with one example of a wound cover.

An alternative embodiment of the invention is shown in FIG. 11, which is a diagrammatic cross-section illustrating the skin 120 of a person having a body-attachable pad 122 of medical grade adhesive material such as that referred to above. The wound of the patient is seen at 124. The hole 123 in the pad 122 has been cut to suitably surround the wound according to the medical requirements. A disc 126 carrying an optional circular rim 128 is connected to the pad 122 by a flexible annular sheet 130. The sheet 130 may be of fabric or of a thin flexible plastics film.

The disc 126 carries a stack of annular plasters 132, each of which has a tab 134. A strippable protective front cover layer 136 protects the adhesive 138 on the outermost plaster. A wound cover 141 having a flat thin plate of annular form 144 co-operates with the body-attachable appliance including the pad 122. In use, the protective layer 136 is stripped off exposing the adhesive layer 138 and the cover 141 is brought in face to face manner up against this adhesive, the rim 128 then extending just within the hole in the plate 144. The cover 141 is consequently prevented from moving sideways relative to the wound during the application of the wound cover. During this application, if desired, fingers can be placed behind the disc 126 to support the disc 126 against the pressure needed to press the cover 141 on, so that the plate 144 contacts the adhesive 138. When desired e.g. when the wound is to be inspected, the cover 141 is removed. The used plaster is also removed so exposing a fresh adhesive surface on the plaster 132 beneath. A new wound cover can then be applied.

Figure 12:
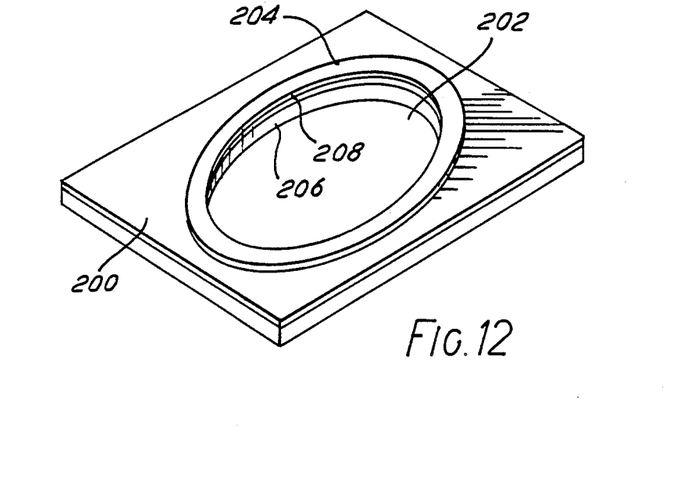
FIG. 12 is a perspective view of a rectangular medical grade adhesive pad intended for surrounding a wound.

FIG. 12 illustrates another example of medical grade adhesive pad which can be used in accordance with the invention. It comprises a rectangular pad 200 which may have a peel-off cover layer (not shown) on its rear surface (the lower surface as seen in the drawing). In use the rear surface is applied to the skin of the wearer surrounding the wound. On its top surface the pad has a plastics film 208. The pad has an oval, generally central, hole 202 therein and around the rim of this hole is a flat annulus 204 of rigid or semi-rigid plastics material, e.g. PVC. The edge of the pad 200 is seen at 206. The purpose of this annulus is to provide a flat smooth surface to which adhesive can bond. The pad according to FIG. 12 can be used with a plaster 210 according to FIGS. 13 and 14. The illustrated adhesive plaster 210 (FIGS. 13 and 14) includes a substrate 212 (which may for example be a conventional fabric substrate as found in conventional sticking plasters) having a central hole therein to register with the hole 202. The rear (body side) surface of the substrate carries adhesive 216 whereby the plaster can be fixed to a body-attachable member 200 (FIG. 12). The front surface carries adhesive 220 which is covered by a peelable protective layer 222. The layer 222 is divided into five annular regions 222a to 222e by circular partial cuts 224 which extend through, for example, about ¾ of the thickness of the protective layer 222. These cuts may be made by a punching or stamping operation. Alternatively the cuts may extend completely through the layer 222, or lines of weakening may be produced by having rows of perforations. Other expedients will occur to a man of average skill in the art.

Figure 13:
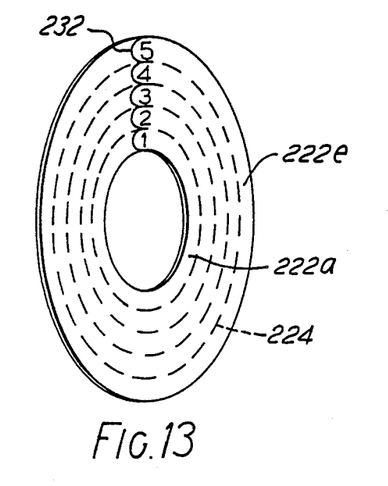
FIG. 13 is a view of an assembly of oval peel-off annuli for use in conjunction with the pad shown in FIG. 12.
Figure 14:
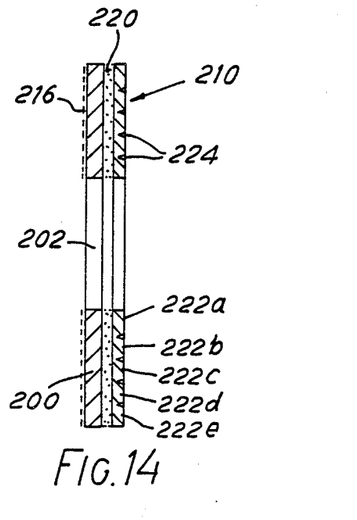
FIG. 14 is a cross-section taken in a vertical plane through an assembly of the parts shown in FIGS. 12 and 13 with the thickness exaggerated for clarity of illustration.

The shape of the hole in the plaster 210 may be chosen at will, and the cuts 224 may be chosen to correspond. A circular configuration of hole and cuts can be employed although oval is suitable for many wounds.

In use, the inner ring 222a is peeled or stripped off, so exposing an annular area of adhesive 220, and a wound cover is brought face to face contact with the exposed area of adhesive 220. To facilitate stripping off the rings 222a to 222e, each ring may carry a tab or projection 232 which can be grasped between finger and thumb. The tabs may if desired be numbered as shown in FIG. 13.

In an advantageous embodiment of the invention, the adhesive 216 (FIG. 14) may be such as to have a higher "peel strength" than the adhesive 220. This ensures that the attachment of the plaster 210 to the pad 18 remain secure when force is applied to peel off one of the rings 222a to 222e.

Figure 15:
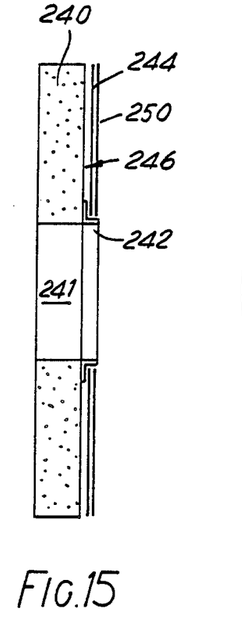
Figure 16:
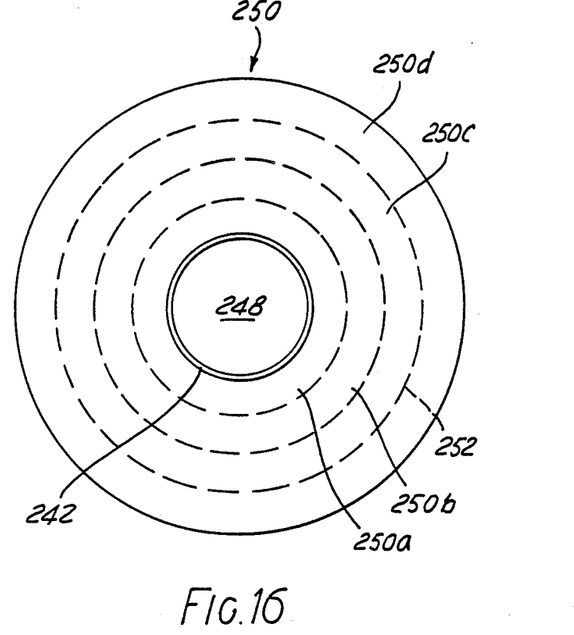

FIG. 15 illustrates a body-attachable medical grade skin-adherable pad 240 which is disc-shaped with a central hole 241, i.e. is annular in shape. To the pad 240 is attached a vacuum formed plastics rim 242. An adhesive plaster 244 according to the invention is directly fixed in any suitable way, e.g. by adhesive, to the front face 246 of the pad 240. The plaster 240, 242 has a central hole 248 of a diameter slightly greater than the outer diameter of the rim 242. A protective layer 250 can be manually peeled or stripped from the plaster 244. The layer 250 is separated by cuts 252 into concentric rings 250a to 250d (FIG. 15). Each of these rings can be separately stripped from the plaster 244. While the plaster 244 and pad 240 are shown as circular in shape, they could have other configurations.

The pad 200 or the pad 240 may be made of a medical grade adhesive as described above.

An advantageous form of body-attachable pad consists of three layers, namely a skin compatible medical grade adhesive, a plastics film thereon, and a Fasson fabric plaster layer covering the film and having its marginal edge portions extending somewhat beyond the outer edges of the adhesive and the film. The adhesive and the film will normally be coextensive. The purpose of the Fasson fabric layer is to shield the edges of the adhesive so that, for example, these edges do not slide to the clothing of the wearer.

Figures 17, 18:
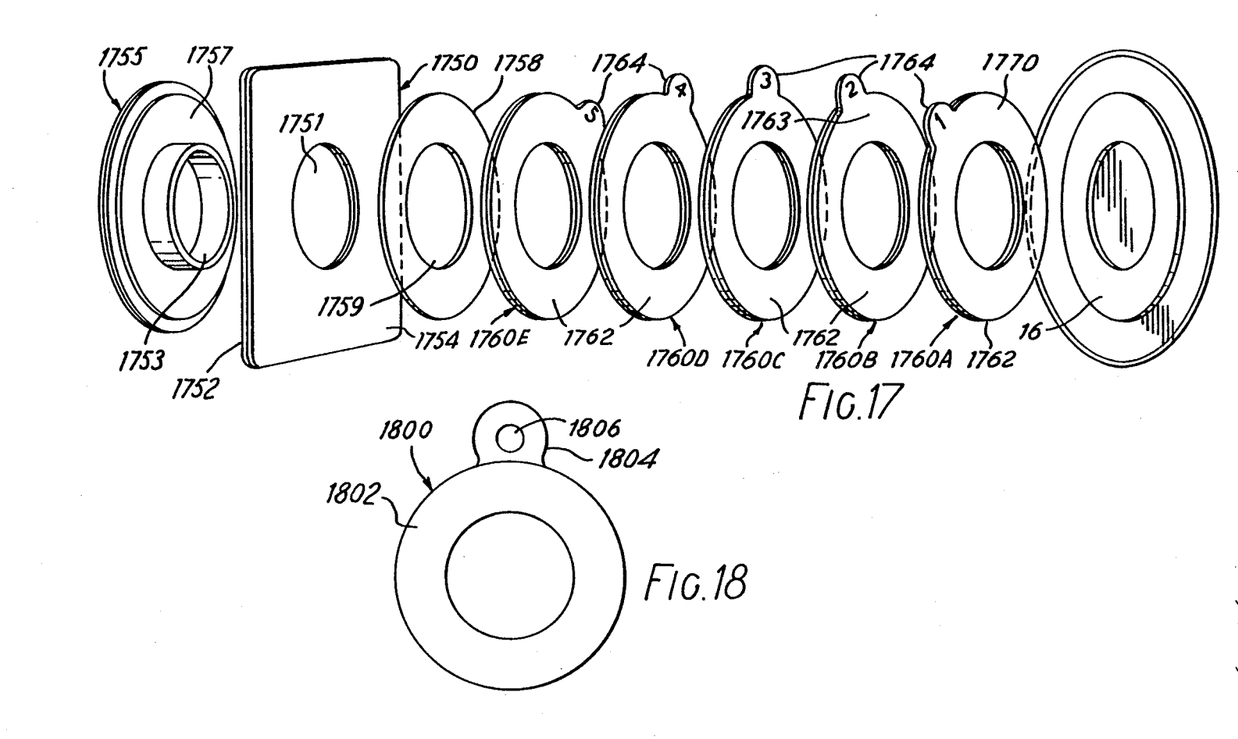
FIG. 17 is an exploded perspective view of a medical grade adhesive pad, a porous adhesive layer, and a plurality of peelable adhesive members with angularly offset projecting tabs.
FIG. 18 is a front elevational view showing in greater detail one of the peelable adhesive members of FIG. 17.

Referring now to FIG. 17, an alternative embodiment of the present invention is shown in exploded view. The wound management appliance includes a flexible microporous attachment patch 1750 having an aperture 1751 therethrough to accommodate a rib 1753 on a medical grade skin-compatible adhesive pad 1755. The diameter of the aperture 1751 is larger than the diameter of rib 1753 but smaller than the diameter of pad 1755. The patch 1750 comprises an adhesive layer 1752 that overlaps the pad 1755 and any outer surface 1754 of the microporous patch is a porous layer.

In FIG. 17, the patch 1750 is larger in area than pad 1755 and square or rectangular in shape. In use adhesive surface 1752 is pressed onto the body a distance from the wound and aids the adhesive pad 1755 in maintaining the wound cover in place.

The term microporous is used in connection with adhesive layer 1752 because layer 1752 appears to be continuous but when viewed under a microscope it is sponge-like having randomly located channels and voids. The layer 1752 can be of the acrylic type as taught by Copeland in U.S. Pat. No. 3,121,021, or it can be made of the same ingredients as pad 1755 with the microporosity resulting from a difference in processing. See European Patent Application No. A1 0081 907. This microporous patch can also be employed as adhesive layer 74 in the embodiment shown in FIGS. 5 to 10.

The porous backing layer 1754 can be formed of woven or non-woven fabric such as the rayon web described by Copeland in U.S. Pat. No. 3,121,021, an open mesh polymeric substance such as an open mesh polyethylene or polypropylene or a polymeric foam such as polyurethane foam, polyethylene foam, etc., or a non-woven material made from polyester fibers, polypropylene fibers, nylon fibers, composite olefin fibers, or cellulose fibers which are commercially available.

The patch 1750 while aiding in attaching the ostomy appliance to the user is flexible and allows the skin to breathe resulting in a more comfortable attachment.

The patch 1750 is affixed to the flange surface 1757 not only by its own adhesive layer 1752 but also by an overlapping member 1758 such as a plastics film having an adhesive layer on each side. Member 1758 has an aperture 1759 therethrough which is slightly larger then the diameter of rib 1753. The outer diameter of member 1758 is larger than the aperture 1751 in patch 1750. Member 1758 overlaps both a portion of flange 1757 adjacent rib 1753 and a portion of surface 1754 of patch 1750.

In FIG. 17, the peelable adhesive members are indicated at 1760, and for example, five are shown, 1760A to 1760E. Each member comprises a layer of tough paper or flexible plastics film bearing an adhesive layer 1762 and having a grippable tab 1764. The tab arrangement is such that each is angularly displaced from the tab of an adjacent member around the common axis of the members 1760. The fifth peelable adhesive member 1760E, the last in order of use (i.e. the one nearest the member 1758), is directly adhesively attached to the outwardly facing adhesive surface of member 1758. It will be remembered that member 1758 comprises a double adhesive layer, one on each side thereof. The non-adhesive surfaces of each of the remaining members (those surfaces which face pad 1755) are attached to the adhesive surface 1762 of the previous member which faces the surface 16 of wound cover 12.

The outermost peelable member 1760A, the first one to be used, has attached thereto a suitable protection cover layer 1770 which protects the outer adhesive layer 1762 of the first member 1760A until use.

FIG. 18 is a front elevational view of a member 1800 suitable for use as member 1760 in FIG. 17 but showing in more detail an alternative embodiment of tab 1762. The member 1800 preferably is made of a clear flexible plastics film with one surface such as the outward facing surface 1802 coated with an adhesive. The member 1800 further comprises a circularly shaped grippable tab portion 1804 having an opening 1806 therethrough. The tab is large enough to be easily gripped by the wearer's fingers and the opening 1806 assists therein.

Figure 19:
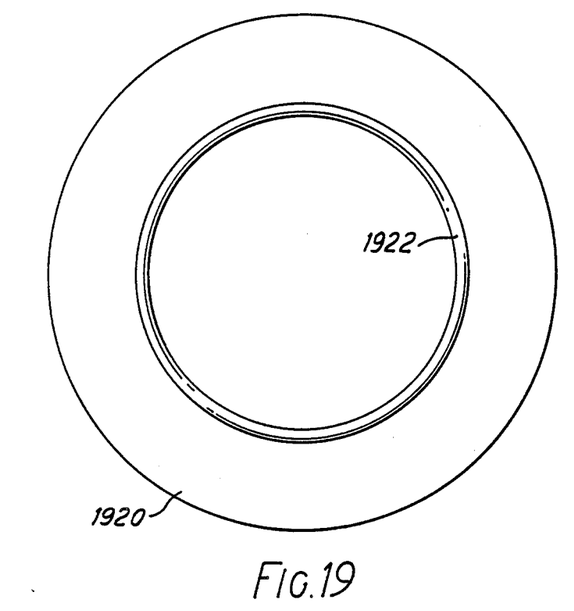
FIGS. 19, 20 and 21 illustrate a tapered or angled rib feature of one embodiment of the present invention, FIG. 19 being a front view, FIG. 20 a vertical axial cross-section, and FIG. 21 being an enlargement of part of FIG. 20.
Figure 20:
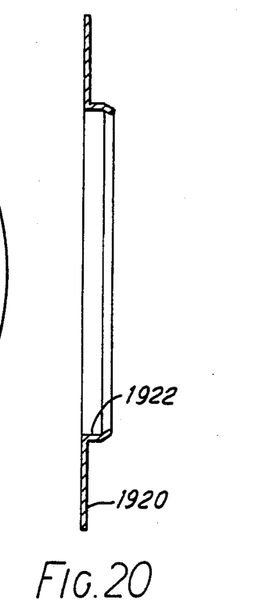
Figure 21:
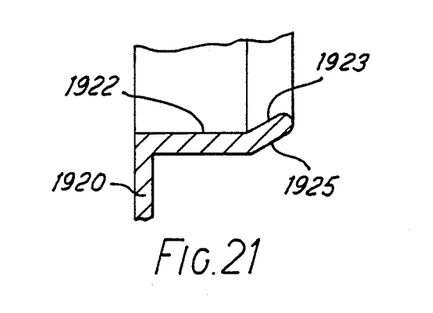

FIGS. 19-21 illustrate an alternative design of a flange member for attachment to the medical grade adhesive pad 10 illustrated in FIG. 1. This flange member 1920, like the flange member 20 of FIG. 1, has an inner peripheral rib 1922. In order to provide a "lead-in" when a user is attaching a bag to an exposed adhesive surface of one of the peelable adhesive members, the inner end, that is to say the end of the rib which extends partly into the wound cover when the cover is being applied, is canted inwardly as seen best in FIG. 21 at 1923. Consequently, a tapered annular outer surface 1925 is provided which assists the fitting of a wound cover.

Figure 22:
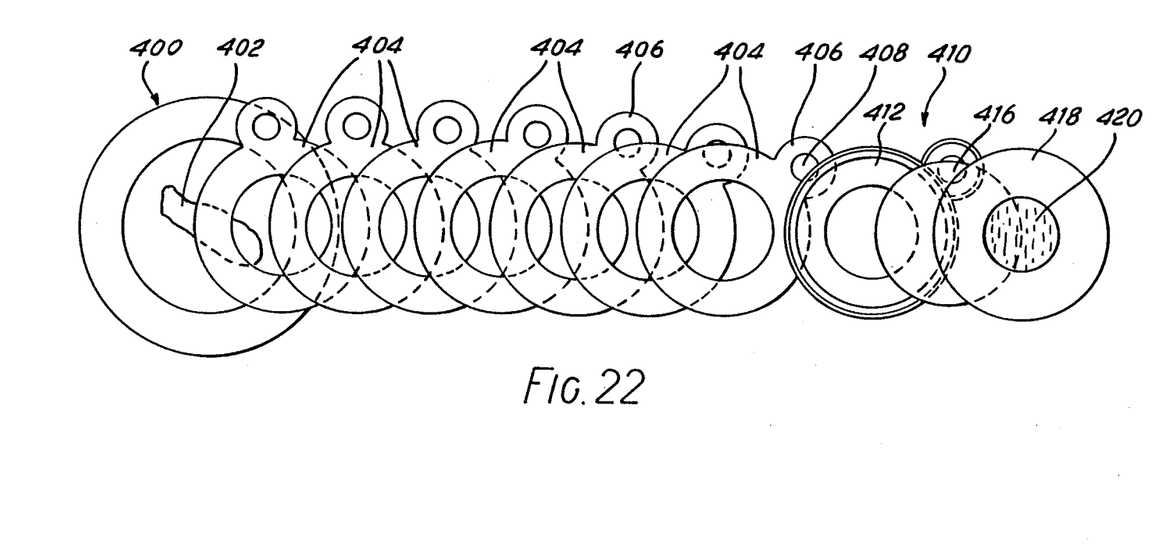
FIG. 22 is an exploded diagrammatic view of another embodiment of wound management device according to the invention.

A further embodiment of the invention is illustrated in FIG. 22.

The arrangement illustrated in FIG. 22 is a diagrammatic exploded view. The illustrated arrangement includes a skin compatible medical grade adhesive pad 400 intended to surround a wound indicated at 402. There are seven individual pull off adhesive annuli, each of these having adhesive on one surface, namely the rear surface as seem in the drawing. These annuli are indicated at 404. Each of them has a pull tab 406 with a hole 408 therein. A wound cover generally indicated at 410 includes a plastics flange 412 with a pull tab 414, an absorbent pad 416, and (as an optional component) a cover film 418 which may have a gas vent means including a filter 420. This is to allow escape of any gases which may be exuded from the wound. While illustrated as of annular configuration, the wound management device illustrated in FIG. 22 may be constructed of other shapes, as may be suitable for the wound concerned.

It will be seen that the various wound management appliances disclosed and illustrated provide a means not hitherto available, whereby a suitable pad can remain undisturbed around a wound and yet access to the wound for inspection or treatment can be repeatedly obtained without dislodging the pad.

The wound cover herein disclosed may include a gas venting means. Such a means may include a filter or equivalent for deodorizing the exiting gases.

What is claimed is:

1. A wound management appliance for treating a wound of a patient comprising:
   a medical grade adhesive pad for attachment to the skin surrounding the wound;
   a plurality of adhesive annuli, one on top of the other and carried by the pad and surrounding the wound, for attaching a plurality of wound covers in sequence to the pad by exposing a fresh region of adhesive each time it is desired to attach a fresh wound cover; and
   a plurality of sequentially peelable cover annuli separating said adhesive annuli.

2. A wound management appliance according to claim 1 in which each peelable cover annulus has a radially projecting finger tab which serves two purposes, firstly it can carry a number or indication and secondly it enables the peelable cover annulus to be readily stripped off to expose the adhesive surface of the underlying double sided adhesive layer.

3. A wound management appliance according to claim 2 in which the tabs are arranged so that peeling off a first tab exposes a second tab, the latter not being accessible to the user until the first tab has been peeled off.

4. A wound management appliance according to claim 2 in which the tabs are radially extending and angularly spaced apart from tabs of adjacent adhesive numbers.

5. A kit of parts for making a wound management appliance including an apertured pad of body-attachable, skin-compatible material, and a plurality of wound covers to each of which is attached a peelable cover layer which when removed exposes an annular region of adhesive on a flange of the wound cover, the said region of adhesive being arranged to be capable of adhesively securing in use, each wound cover in turn to the pad.

6. The appliance of claim 1 wherein said adhesive annuli comprise double sided adhesive annuli.

* * * * *